United States Patent [19]
Nolan

[11] Patent Number: 6,063,071
[45] Date of Patent: *May 16, 2000

[54] METHOD FOR CORNEAL RESURFACING

[76] Inventor: Gerard Michael Nolan, 565 Waterville Rd., Avon, Conn. 06001

[*] Notice: This patent issued on a continued prosecution application filed under 37 CFR 1.53(d), and is subject to the twenty year patent term provisions of 35 U.S.C. 154(a)(2).

[21] Appl. No.: 08/797,538

[22] Filed: Feb. 7, 1997

[51] Int. Cl.[7] ................................................. A61N 5/06
[52] U.S. Cl. .......................... 606/4; 606/2; 606/10; 606/13; 604/19; 607/89
[58] Field of Search ................... 606/2, 3–6, 10, 606/13–19; 607/88–92; 604/19

[56] References Cited

U.S. PATENT DOCUMENTS

| | | | |
|---|---|---|---|
| 4,461,294 | 7/1984 | Baron | 606/5 |
| 5,019,074 | 5/1991 | Mullen | 606/5 |

*Primary Examiner*—David M. Shay
*Attorney, Agent, or Firm*—Reed Smith Shaw & McClay LLP

[57] ABSTRACT

A method for treating a corneal abnormality. A marked corneal surface is formed by applying a pigment to an outer surface of the cornea over the corneal abnormality. The marked corneal surface is preferably centered about the corneal abnormality. Thereafter, the marked corneal surface is illuminated with laser light for a period sufficient to treat the corneal abnormality.

23 Claims, 2 Drawing Sheets

METHOD FOR CORNEAL RESURFACING

FIELD OF THE INVENTION

The present invention relates generally to the field of corneal resurfacing. More particularly, the present invention relates to laser-based procedures for corneal resurfacing. Still more particularly, the present invention relates to a laser-based corneal resurfacing procedure for treatment of recurrent corneal erosion and other abnormalities.

BACKGROUND OF THE INVENTION

Recurrent corneal erosion typically occurs in eyes that have suffered a sudden sharp, abrading injury (e.g., fingernail, edge of paper, etc.). The superficial injury produces an epithelial abrasion which heals rapidly, leaving no clinical evidence of damage. After an interval varying from days to years, symptoms suddenly recur in the absence of any obvious cause. In most instances they again subside promptly, only to recur periodically. In contrast to shearing injuries, small and partially penetrating foreign bodies which strike the cornea directly and become embedded in the epithelium or superficial stroma rarely produce recurrent erosions. Some patients recall no injury and have an inherited potential for superficial degeneration of the cornea (i.e., basement membrane disease).

Repeated episodes of foreign body sensation, tearing, photophobia, and pain describe recurrent corneal erosion which has been a most frustrating condition to treat. These episodes mainly occur in the early morning hours upon awakening. However, these episodes can occur at any other time of day as well. A classic example would be trauma to the cornea by a tree branch or fingernail. When the epithelium attempts to heal over, the epithelium does not heal well and the cells slough off. However, this can occur in a non traumatic eye as well. The poor adhesions on the epithelium are caused by deeper adhesions in the cornea.

Objective signs of recurrent corneal erosion vary from a localized roughening of the epithelium to a true abrasion. The less severe corneal signs resolve rapidly; and often, when the patient is examined within hours of an acute recurrence, no abnormality is discernible. It is recognized that the corneal epithelium is loosely attached to its basement membrane and to Bowman's layer, both at the time of a recurrent attack and between attacks when the cornea appears to be entirely healed.

The first and most common treatment for recurrent corneal erosion is the consistent use of lubricating ointment and frequent instillation of artificial tear drops. Patching is also useful. Also, because of the frequent occurrence of these episodes further methods of treatment are used. Bandage contact lenses have been used with some success as well, but they have been associated with infectious keratitis. Superficial epithelial keratectomy or scraping of Bowman's layer has been somewhat effective, but these treatments have also resulted in multiple spontaneous corneal erosions. As with anterior stromal puncture, such treatment involves making multiple penetrations into the anterior corneal stroma in order to generate secure adhesions between the epithelium and the deeper corneal structures. Drawbacks of this procedure include the risk of perforation, and patient apprehension that results when the patient is approached with a needle while sitting at the slit lamp.

Yag lasers are also used as a form of treatment for recurrent corneal erosion. With each laser application, a small bubble is formed beneath the epithelium. However, if the application is placed too posteriorly, a small stromal lesion occurs. Conversely, if the application is placed too anteriorly, a spark will be seen in front of the cornea.

The Excimer laser has also been shown to be effective in treating corneal erosions. With this procedure the entire corneal surface is lasered leaving the nerves exposed which is extremely painful for the patient. This technique is also much more expensive for the physician to perform as well as for the patient to recompense.

It is an object of the present invention to provide an improved procedure for treating recurrent corneal erosion that does not suffer from the drawbacks of prior treatment methods.

In particular, it is object of the present invention to provide an effective treatment for corneal erosion that is relatively painless for the patient, causes minimal patient apprehension, and minimizes the risk of collateral injury to the eye as a result of the treatment.

It is a still further object of the present invention to provide an effective treatment for recurrent corneal erosion that can be performed relatively quickly and at a reasonable cost to the patient.

It is a still further object of the present invention to provide an effective treatment for eye abnormalities other than those relating to recurrent corneal erosion. For example, it is an object of the present invention to provide alternative treatments for patients suffering from swelling of the cornea or from bullous keratopathy.

It is a still further object of the present invention to provide a general method for illuminating an epithelium layer with laser light without damaging the underlying tissue layers beneath the epithelium. The epithelium layer treated may be on the cornea, or alternatively at some other site on the body.

These and other objects and advantages of the invention will become more fully apparent from the description and claims which follow or may be learned by the practice of the invention.

SUMMARY OF THE INVENTION

The present invention is directed to a method for treating a corneal abnormality. A marked corneal surface is formed by applying a pigment to an outer surface of the cornea over the corneal abnormality. The marked corneal surface is preferably centered about the corneal abnormality. Thereafter, the marked corneal surface is illuminated with laser light for a period sufficient to treat the corneal abnormality.

BRIEF DESCRIPTION OF THE DRAWINGS

In order that the manner in which the above-recited and other advantages and objects of the invention are obtained can be appreciated, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode thereof will be described and explained with additional specificity and detail through the use of the accompanying drawings.

DETAILED DESCRIPTION OF THE PREFERRED EMBODIMENT

Figure 1:
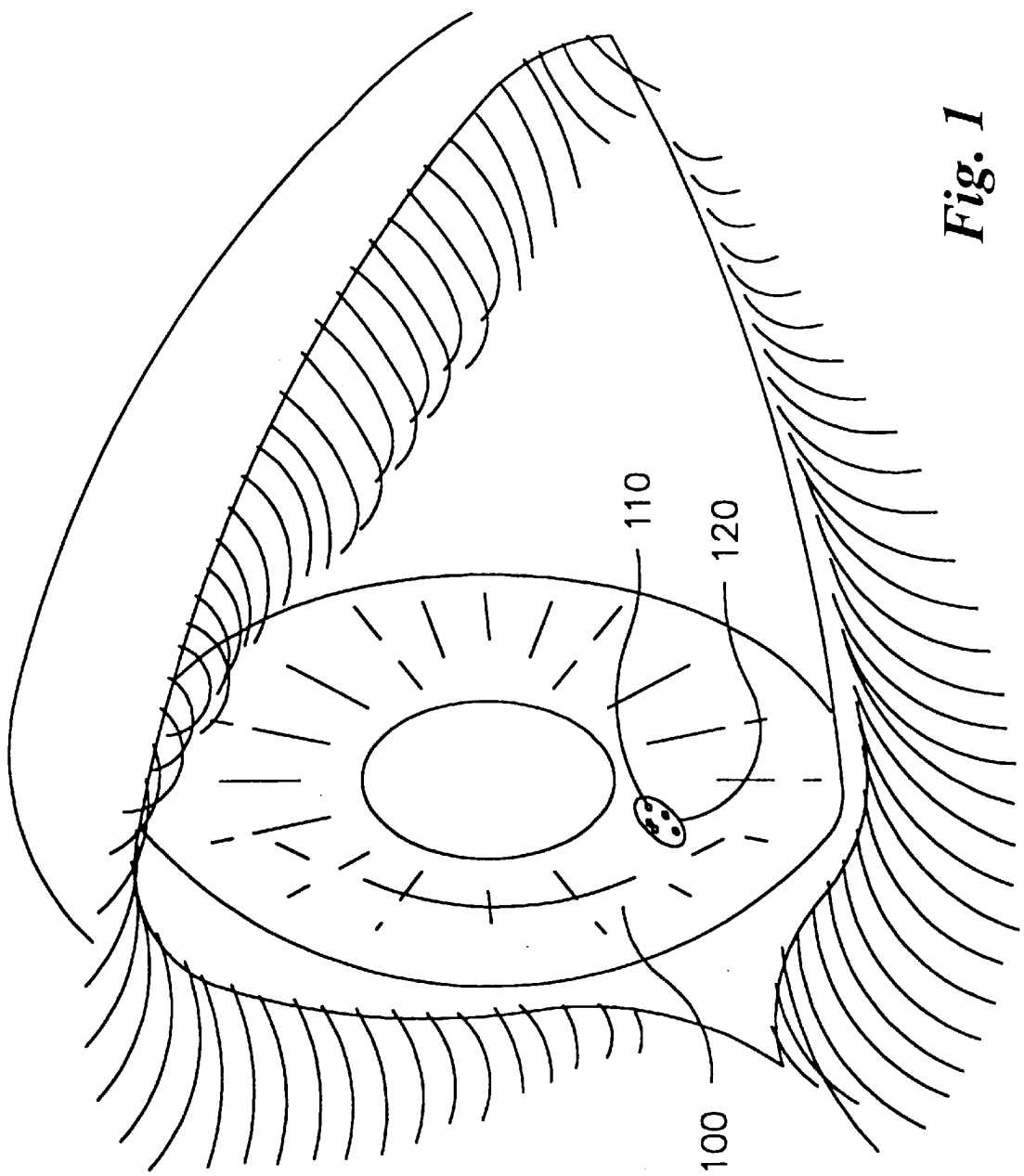
FIG. 1 is a side view of a corneal surface with a plurality of abnormalities that have marked with a pigment, in accordance with a preferred embodiment of the present invention.

Reference will now be made to the drawings wherein like structures are provided with like reference designations. It will be understood that the drawings included herewith only provide diagrammatic representations of the presently preferred structures of the present invention and that structures falling within the scope of the present invention may include structures different than those shown in the drawings.

Figure 2:
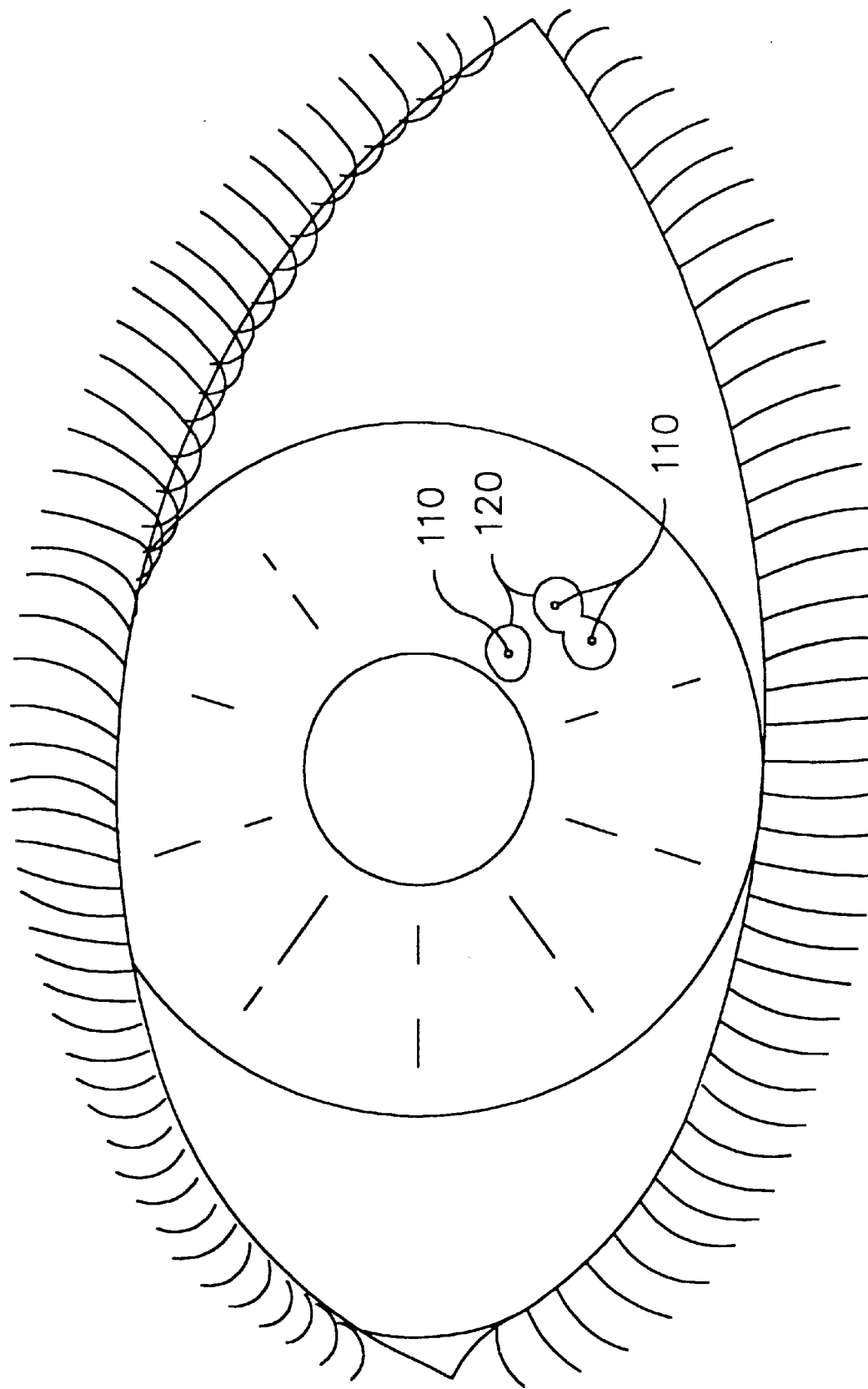
FIG. 2 is a front view of a corneal surface with a plurality of abnormalities that have marked with a pigment, in accordance with a preferred embodiment of the present invention.

Referring now to FIGS. 1 and 2, there are shown side and front views, respectively, of a corneal surface 100 with a plurality of abnormalities 110 that have marked with a green pigment, in accordance with a preferred embodiment of the present invention. Corneal surface 100 corresponds to the epithelium or outer surface of the cornea. Abnormalities 110 correspond, for example, to localized roughening or abrasions on the epithelium which occur in connection with recurrent corneal erosion.

Prior to treatment of a patient having abnormalities 110, a topical anesthesia (e.g., tetracane 1%) is first placed in the patient's eye. The topical anesthesia is preferably first dropped on a pledget which is then applied to the cornea for approximately thirty seconds. Alternatively, the topical anesthesia may be dropped directly into the eye, after which a pledget is applied to the cornea for approximately thirty seconds. The use of the anesthesia in combination with the pledget serves to numb the eye and make the cornea more hydrophilic (and therefore more receptive to the pigment described below).

Thereafter, a plurality of marked corneal surfaces 120 are formed by applying a pigment (shown in green in FIGS. 1 and 2) to corneal surface 100 over each of the corneal abnormalities 110. The pigment is preferably applied directly to the epithelium or outer surface of the cornea by contacting either an autoclaved applicator (such as a pin head) which has been dipped in pigment, an ink pad, a brush which has been dipped in pigment, or a pencil or crayon which carries the pigment, to the epithelium or outer surface of the cornea. In the embodiment shown in FIG. 1, a single marked corneal surface 120 covers several different corneal abnormalities 110. In the preferred embodiment shown in FIG. 2, each marked corneal surface 120 is centered about a corresponding corneal abnormality 110, and the marked corneal surfaces 120 may be non-overlapping or partially overlapping. In the embodiment shown in FIG. 2, each marked corneal surface 120 preferably has an outer radius of 0.5 to 2.5 mm measured from the center of a corneal abnormality 110. In an alternative embodiment (not shown), the pigment may be applied so as to cover the entirety of surface 100.

Following application of the pigment, each marked corneal surface 120 is illuminated with laser light for a period sufficient to treat the underlying corneal abnormality 110. In a particularly preferred embodiment, a coherent argon laser with a spot size of 50–100 microns is used to perform this lasering step. When this laser is used to treat corneal abnormalities resulting from recurrent corneal erosion, the laser light is preferably applied to the pigment over each abnormality 110 for a period of 0.1 to 0.2 seconds/spot at a power level of 200–400 milliwatts. During this lasering step, the pigment used to form the marked surfaces 120 acts as a site positioned proximate to the outer corneal surface for receiving and absorbing laser light energy that would otherwise simply pass through the normally transparent cornea. As a result of this pigment which acts as a receptor for the laser light, the laser light used for illuminating the marked areas 110 is preferably transmitted to the outer surface 100 and then only a small amount into the depth of the cornea. In a preferred embodiment, the laser light reaches a depth corresponding to less than 5% of the thickness of the cornea. The marked areas 120 are preferably allowed to become desiccated prior to illumination of the marked areas 120 with laser light as described above.

In a particularly preferred embodiment, light emitted from a slit lamp is used to darken the pigment on marked areas 120, thereby making the areas 120 even more receptive to laser light during the lasering step described above. In this embodiment, a green filter may be used to color light from the slit lamp. The colored light from the slit lamp is then aimed at the marked areas 120 while simultaneously illuminating the marked areas with the laser light as described above.

The pigment used for forming marked areas 120 is preferably formed from a brilliant green ink, such as Indian ink. In a particularly preferred embodiment, the pigment used represents a mixture of 10% methyline blue and 10% brilliant green ink. It will be understood by those skilled in the art that other pigments (or pigment mixtures) may alternatively be used. The pigment chosen should be such that it will be receptive to laser light when applied to the outer corneal surface. In a particularly preferred embodiment, the pigment is combined with an antibiotic before being applied to the cornea.

The procedure described above has been used to successfully treat three patients having recurrent corneal erosion. The procedure was painless for the three patients, caused minimal patient apprehension, and involved virtually no risk of collateral injury to the eye. Following application of procedure, each of the three patients healed without a patch in 1–4 days.

Although the present invention has been described in connection with a treatment for abnormalities which occur in connection with recurrent corneal erosion, it will be understood by those skilled in the art that the procedure of the present invention may be used to treat or repair corneal abnormalities or abrasions resulting from other conditions such as primary basement membrane disease or bullous keratopathy, or as an alternative treatment for patients requiring a corneal transplant. It is also believed that the method of the present invention may be applied to treat abnormalities on epithelium layers at other sites on the body beyond the cornea, without damaging the underlying tissue layers beneath the epithelium.

Furthermore, it is to be understood that although the present invention has been described with reference to a preferred embodiment, various modifications, known to those skilled in the art, may be made to the structures and process steps presented herein without departing from the invention as recited in the several claims appended hereto.

What is claimed is:

1. A method for treating recurrent corneal erosion, comprising the steps of:
   (A) forming a marked corneal surface by applying a pigment to an outer surface of a cornea over a site associated with said recurrent corneal erosion, wherein said marked corneal surface is centered about and covers said site, and wherein said marked corneal surface has an outer perimeter that is 0.5 to 2.5 mm away from a center of said site; and
   (B) illuminating said marked corneal surface with laser light for a period sufficient to treat said recurrent corneal erosion;

wherein said laser light is transmitted through said outer surface to a depth in said cornea during said illuminating step, said depth being limited to less than 5% of a thickness of said cornea; and whereby no tissue is removed from said outer surface of said cornea during said illuminating step (B), and said cornea has a shape of curvature prior to said illuminating step (B) and said shape of curvature of said cornea is substantially retained following said illuminating step (B).

2. The method of claim 1, wherein said applying step further comprises applying said pigment over an entirety of said outer surface of said cornea.

3. The method of claim 1, wherein said applying step further comprises contacting said outer surface of said cornea with a pin-head sized applicator carrying said pigment in order to apply said pigment to said outer surface of said cornea.

4. The method of claim 1, wherein said applying step further comprises contacting said outer surface of said cornea with an ink pad in order to apply said pigment to said outer surface of said cornea.

5. The method of claim 1, wherein said applying step further comprises using a brush for applying said pigment to said outer surface of said cornea.

6. The method of claim 1, wherein said applying step further comprises using a pencil for applying said pigment to said outer surface of said cornea.

7. The method of claim 1, wherein said applying step further comprises using a crayon for applying said pigment to said outer surface of said cornea.

8. The method of claim 1, wherein said pigment is mixed with an antibiotic before being applied over said corneal abnormality in step (A).

9. The method of claim 1, further comprising the step of, prior to step (B), allowing said marked corneal surface to be become desiccated.

10. The method of claim 1, further comprising illuminating said marked corneal surface with filtered light while simultaneously illuminating said marked corneal surface with said laser light, wherein said filtered light and said laser light travel along different optical paths before reaching said marked corneal surface.

11. The method of claim 1, wherein said corneal abnormality corresponds to an abnormality resulting from recurrent corneal erosion.

12. The method of claim 1, wherein said pigment is formed from Indian ink.

13. The method of claim 1, wherein step (A) comprises forming a plurality of marked corneal surfaces by applying said pigment over a plurality of corneal abnormalities, step (B) comprises illuminating each of said marked corneal surfaces with laser light for a period sufficient to treat each of said corneal abnormalities, and wherein each of said marked corneal surfaces is centered about a corresponding one of said corneal abnormalities.

14. The method of claim 13, wherein said marked corneal surfaces are partially-overlapping.

15. The method of claim 13, wherein said marked corneal surfaces are non-overlapping.

16. The method of claim 1, wherein step (B) further comprises illuminating said marked corneal surface with laser light from a coherent argon laser.

17. The method of claim 16, wherein said coherent argon laser has a spot size of 50 to 100 microns, and said period ranges from 0.1 to 0.2 seconds/spot.

18. The method of claim 1, wherein said pigment is formed from brilliant green ink.

19. The method of claim 18, wherein said pigment is formed from a mixture of methyline blue and brilliant green ink.

20. The method of claim 19, wherein said pigment is formed from a mixture of 10% methyline blue and 10% brilliant green ink.

21. The method of claim 1, further comprising the step of, prior to step (A), applying a topical anesthesia to said outer surface of said cornea.

22. The method of claim 21, wherein said topical anesthesia is applied using a pledget.

23. The method of claim 22, wherein said outer surface of said cornea is hydrophilic after said topical anesthesia is applied using said pledget.

* * * * *